United States Patent
Van Den Honert et al.

(10) Patent No.: US 8,412,341 B2
(45) Date of Patent: *Apr. 2, 2013

(54) METHOD AND APPARATUS FOR OPTIMIZING THE OPERATION OF A COCHLEAR IMPLANT PROSTHESIS

(75) Inventors: Chris Van Den Honert, Aurora, CO (US); Ernst Ludwig Von Wallenberg, Muelheim (DE); Norbert Dillier, Kusnacht (CH); Wai Kong Lai, Zurich (CH); Jochen Nicolai, Basel (CH); Mathias Stecker, Soelden (DE); Joachim Mueller-Delle, Kiel (DE); Denise Cafarelli Dees, Hants (GB); Roland Laszig, Freiburg (DE)

(73) Assignee: Cochlear Limited, Macquarie University, NSW (AU)

( * ) Notice: Subject to any disclaimer, the term of this patent is extended or adjusted under 35 U.S.C. 154(b) by 1519 days.

This patent is subject to a terminal disclaimer.

(21) Appl. No.: 10/856,823

(22) Filed: Jun. 1, 2004

(65) Prior Publication Data

US 2005/0107844 A1  May 19, 2005

Related U.S. Application Data

(62) Division of application No. 09/936,455, filed as application No. PCT/AU00/00148 on Mar. 31, 2000, now Pat. No. 6,751,505.

(30) Foreign Application Priority Data

Mar. 3, 1999 (AU) .......................................... PP8991
Aug. 27, 1999 (AU) ....................................... PQ2499

(51) Int. Cl.
*A61N 1/36* (2006.01)

(52) U.S. Cl. ........................................... 607/57; 607/62
(58) Field of Classification Search .............. 607/55–57, 607/62; 600/559
See application file for complete search history.

(56) References Cited

U.S. PATENT DOCUMENTS

| | | | |
|---|---|---|---|
| 4,612,934 A | 9/1986 | Borkan | |
| 4,648,403 A * | 3/1987 | Van Compernolle | 607/57 |
| 5,143,081 A | 9/1992 | Young et al. | |
| 5,597,380 A | 1/1997 | McDermott et al. | |
| 5,603,726 A | 2/1997 | Schulman et al. | |
| 5,758,651 A | 6/1998 | Nvaard et al. | |
| 5,938,691 A | 8/1999 | Schulman et al. | |
| 5,991,663 A | 11/1999 | Irlicht et al. | |
| 6,205,360 B1 * | 3/2001 | Carter et al. | 607/57 |
| 6,289,247 B1 * | 9/2001 | Faltys et al. | 607/57 |
| 6,600,955 B1 | 7/2003 | Zierhofer | |

FOREIGN PATENT DOCUMENTS

| | | |
|---|---|---|
| WO | WO 94/14376 | 7/1994 |
| WO | WO 97/09863 | 3/1997 |
| WO | WO 97/48447 | 12/1997 |

(Continued)

OTHER PUBLICATIONS

EP 00 906 083.1-1265 Search Report, Apr. 26, 2005, Cochlear Limited.

(Continued)

*Primary Examiner* — Scott M Getzow
(74) *Attorney, Agent, or Firm* — Kilpatrick, Townsend & Stockton, LLP.

(57) ABSTRACT

Disclosed is a method and apparatus for controlling the operation of a Cochlear implant prosthesis to optimize the effect of stimulation for a given patient. The optimal operation mode is determined in accordance with predetermined parameters measured from the neural response of the patient's auditory system in response to a neural stimulation.

55 Claims, 3 Drawing Sheets

FOREIGN PATENT DOCUMENTS

| WO | 9836711 | 8/1998 |
| WO | 9836795 | 8/1998 |
| WO | WO 99/66982 | 12/1999 |

OTHER PUBLICATIONS

Abbas, et at. "Summary of Results Using the Nucleus C124M Implant to Record the Electrically Evoked Compound Action Potential" *Ear & Hearing*, Feb. 1999, vol. 20, No. 1, pp. 45-59.

Haenggell et al., "Electrically Evoked Compound Action Potential (ECAP) of the Cochlear Nerve in Response to Pulsatile Electrical Stimulation of the Cochlea in the Rat: Effects of Stimulation at High Rates," *Audiology*, 1998; 37: 353-371.

Abbas, et al., "Summary of Results Using the Nucleus C124M Implant to Record the Electrically Evoked Compound Action Potential," Ear & Hearing 1999;20; p. 45-59.

Shallop et al, Neural Response Telemetry with the Nucleus CI24M Cochlear Implant; Laryhgoscope 109; Nov. 1999, pp. 1755-1759; Lippinpott Wms & Wms; Philadelphia, PA.

Hanekom et al; Gap Detection as a Measure of Electrode Interaction in Cochlear Implants; Acoustical Society of America; Oct. 1998; pp. 2372-2384; vol. 104, No. 4; J. Acoust. Soc. America.

Cohen et al; Spatial Spread of Neural Excitation in Cochlear Implant Recipients etc.; Hearing Research; Mar. 2003; pp. 72-87; vol. 179; Elsevier Science B.V.

EPO Search Report. EP 06 02 1160. Mailed Jan. 30, 2007.

* cited by examiner

METHOD AND APPARATUS FOR OPTIMIZING THE OPERATION OF A COCHLEAR IMPLANT PROSTHESIS

CROSS-REFERENCE TO RELATED APPLICATIONS

The present application is a divisional of and claims priority from co-pending U.S. application Ser. No. 09/936,435, entitled, "Method and Apparatus for Optimising the Operation of a Cochlear Implant Prosthesis," filed Apr. 30, 2002, which is a national stage application of PCT/AU00/00148 filed Mar. 3, 2000, and that claims priority of Australian Provisional Patent Application No. PP8991, filed Mar. 3, 1999, and Australian Provisional No. PQ 2449, filed Apr. 27, 1999, the entire contents and specifications of which is hereby incorporated by reference.

BACKGROUND

1. Field of the Invention

The present invention relates to cochlear implant prostheses and in particular to a method and apparatus for adjusting the operation of such a prosthesis in order to optimize the benefit of the therapy provided by the prosthesis to a user.

2. Related Art

It is known that individual patients using a cochlear implant system differ in their ability to benefit from different speech coding strategies. These coding strategies may differ in the number of channels activated, the dynamic or fixed allocation of channels to electrodes and the rate of stimulation for each channel. For example, some patients show significant improvements in open-set speech understanding when converting from a relatively low rate of stimulation of 250 Hz per channel (for example as provided by the SPEAK stimulation strategy used in some of the products manufactured by the Cochlear Limited, NSW, AU) to rates of 1200 Hz per channel or more (for example as provided by the ACE stimulation strategy also used in some of the products manufactured by the Cochlear Limited, NSW, AU) while other stimulation parameters, such as the number of channels and their allocation to electrodes remain unchanged. Other patients show no improvement, or even a reduction in benefit, when the stimulation rate is increased from low rates to high rates.

Consequently at present the adjustment of operation of the implant in order to optimize the benefit of the therapy provided to a patient by a cochlear implant prosthesis is to some extent a hit-or-miss affair. In particular comments must be sought from the patient as to whether or not the benefit of the prosthesis is improved or decreased upon making an adjustment in operation. There are a number of problems associated with this prior art approach. For example the adjustment is not made according to any quantitative parameter but rather is based on the somewhat subjective judgments of the patient.

Furthermore some patients, for example young children, may not be able to readily indicate an improvement or decrease in the quality of their hearing perception during the adjustment process. Yet a further problem is that the present approach does not readily lend itself to automation, relying as it does on the conscious feedback of the patient. It is an object of the present invention to provide a method for setting a cochlear implant prosthesis to an appropriate operation mode which overcomes the previously described problems.

SUMMARY OF THE INVENTION

According to a first aspect of the invention, there is provided a method for adjusting the operation of a cochlear implant prosthesis, comprises a) recording at least one neural response in respect of at least one electrode of said cochlear implant prosthesis; b) determining a selected parameter from said recording; c) determining an optimum operation mode for said cochlear implant prosthesis selected on the basis of said selected parameter; and d) adjusting the operation of said cochlear implant prosthesis to operatively cause said cochlear implant prosthesis to operative in said optimum operation mode.

According to another aspect of the invention, a system for adjusting the operation of a cochlear implant prosthesis, comprises a processor configured to cause the prosthesis to stimulate an auditory system so as to evoke neural responses, and further configured to analyze the neural responses in order to determine an optimal operation mode dependent on at least one selected parameter derived from the neural responses and to cause the prosthesis to operate in the optimal mode.

DETAILED DESCRIPTION

Neural Response Telemetry (NRT) is well known in the art. For example an NRT system in the context of a cochlear prosthesis is described in U.S. Pat. No. 5,758,651, hereby incorporated by reference herein. It has been found that various neural response measurements carry a wealth of information about the behavior of the auditory nerve fibers in response to electrical stimulation. As such, many different forms of measurement may be made, which in turn may lead to adjustment of varying operating parameters of an auditory prosthesis according to the needs and capacities of an individual user.

Figure 1A:
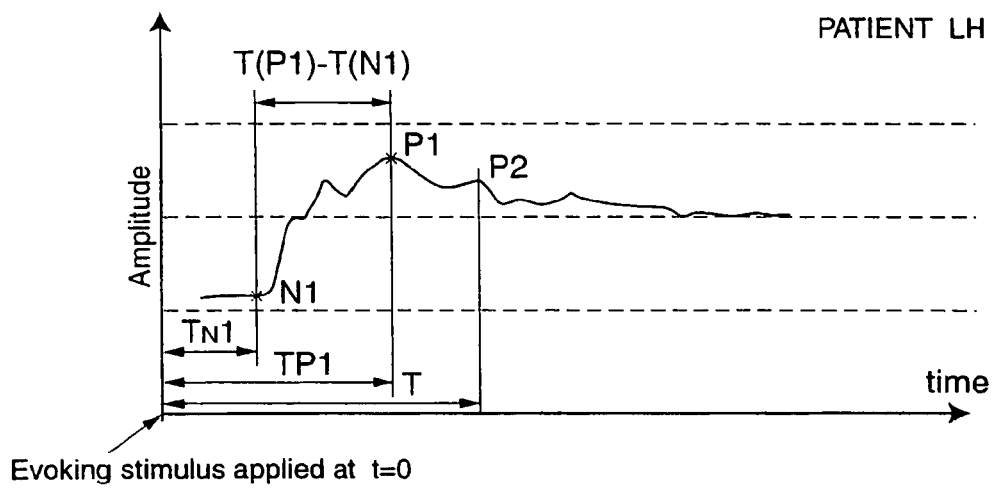
FIG. 1A illustrates a neural response waveform recorded in respect of a first patient.
Figure 1B:
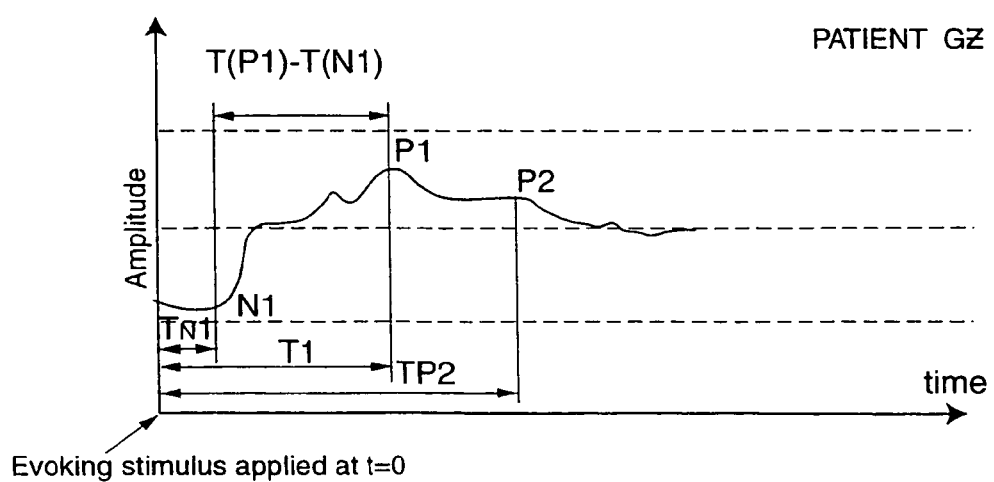
FIG. 1B is a graph of a neural response waveform recorded in respect of a second patient.

In the context of this application and as can be seen in FIGS. 1A and 1B, a neural response whose properties are to be measured comprises an electrical potential which varies with time (producing a "waveform") and is generated by activity within the fibers of the auditory nerve or cochlear nucleus. Most commonly, an individual waveform comprises a peak of negative potential (usually termed N1), sometimes followed by a peak of positive potential (usually termed P1), followed by a return to baseline (approximately zero potential). In some cases, a peak of positive potential (P2) may precede the N1 peak. However, the waveform morphology may differ due to variations in recording electrode geometry or position, underlying neural synchrony, or pathological condition of the nerve fibers. Individual waveforms are often characterized by "magnitude" which refers to the potential difference between some feature of the waveform (for example N1 peak) and another (for example the P1 peak or the baseline). Such magnitudes depend upon a number of conditions such as the number of fibers activated, their synchrony, the strengths of the individual fiber activities, and the geometric relationships among the fibers and the recording electrodes (including distances and angles).

Such waveforms can be measured from electrodes positioned within or near the cochlea. An electrode of an apparatus for measuring such potentials is disclosed in previously referenced U.S. Pat. No. 5,758,651. However other apparatus, not necessarily incorporated within the prosthesis itself, may also be used to perform such a measurement.

Generally, measurement of the neural response involves: a) delivery of an electrical stimulus current through a set of two or more electrodes which current activates some or all fibers of the auditory nerve, and b) subsequent recording of the ensuing electrical potential signals generated by the activated fibers. The recording may be performed using the same electrodes which carried the stimulus, or different electrodes. The electrodes used to perform the recording must be within or in the immediate vicinity of the cochlea (ie not on the scalp).

In its simplest form, the measurement is performed using a single excitatory current pulse (for example a biphasic current pulse) as a stimulus, followed by a measurement of a single potential waveform which constitutes the neural response. More generally, the stimulus may comprise a complex sequence of electrical current waveforms and the response may similarly comprise a sequence of potential waveforms generated by the fibers of the auditory nerve. An example of a slightly more complex sequence is the presentation of two equal-intensity stimulus current pulses in rapid succession, and the recording of two potential waveforms, one in response to each pulse. A still more complex stimulus may comprise a sequence of multiple current pulses of varying intensity. In this case, the neural response may be a similar sequence of potential waveforms, each following one of the pulses, or alternatively each associated with some feature of the stimulus such as a maximum in its intensity envelope.

For simplicity, the use of the term "pulse" will refer to a component of a stimulus. However, it should be clear that the term "pulse" is not restricted to any particular wave shape such as a biphasic rectangular pulse. It refers more generally to any momentary variation in current which constitutes a subcomponent of an overall stimulus. A stimulus may comprise a single "pulse" or a long and complex sequence of many "pulses".

The entire stimulus may be delivered through a single set of electrodes, or different pulses may be delivered through different sets of electrodes. For example, a sequence of three pulses may be delivered through a single pair of electrodes, or alternatively, a different pair of electrodes may be selected for delivery of each pulse of the stimulus. Similarly, the entire response may be measured from a single set of electrodes, or a sequence of potentials measured using different recording electrodes for each potential. Some or all of the electrodes used for delivery of the stimulus may also be used for recording the response, and some or all of the electrodes may be used to deliver the stimulus. Alternatively, the electrode sets used for stimulation and recording may be completely separate.

The particular stimulus to be employed is determined by the response property of interest as would be understood by one skilled in the art.

Regardless of the particular stimulus employed, signal averaging may be used to improve the clarity of the recorded potential waveforms (responses). This process involves repeating the entire stimulus and recording process two or more times using the identical stimulus each time, and then averaging the two or more resulting responses together. Such averaging serves to reduce the noise in the response and is a well known method.

The response properties of interest will include neural response properties, which could fall into three possible categories. For example, these categories could be temporal properties, spatial properties and spatio-temporal properties.

Temporal properties of the neural response depend upon timing between various features of the stimulus or various features of the response waveforms, or both. Often, these properties are also characterized by response waveform magnitude and its dependence on such timing, or on stimulus intensity, or both. Examples of temporal properties and relationships which may be used to quantify each of these properties include:

1. Latency—
latency is the time delay from onset or offset of a stimulus (or other feature of the stimulus such as a envelope maximum) to the occurrence of a particular response feature such as the N1 peak or P1 peak.
This property can be quantified by a relationship such as Latency (L)=tz−$t_i$, where $t_1$ is the time at which a stimulus begins, and tz is the time at which the $N_1$ peak of the response occurs.

2. Integration—
integration refers to the effective summation of two or more stimulating pulses occurring in rapid succession which, acting in concert, achieve more effective stimulation than if each were presented alone. For example, a sequence of two or more pulses presented in rapid succession may generate a response waveform with a greater magnitude than would be generated by either individual pulse alone. Integration may be characterized by the measured relationship between interpulse interval and waveform magnitude. Alternatively, it may be characterized by the measured relationship between interpulse interval and stimulus intensity required to achieve a specified response waveform magnitude. Many other parametric relationships may also readily defined to characterize integration.

One possible way of quantifying the property of integration is to consider that it can be characterized by parameter U in the equation:

$$Q(t)=Mo(1+e^{-t/u})$$

Where U is determined by a curve fitting procedure which minimizes the error between the function Q(t) and a sequence of n parameters $Q_1, Q_2, \ldots Q_n$ determined for a sequence of n delay values $t_1, t_2, \ldots t_n$. In each case, $$Q_i + M_i/M_o$$

Where Mo is the magnitude of a response elicited by a single stimulus presented in isolation, and Mi is the magnitude of a response elicited by two identical stimuli presented in rapid succession separated by delay $t_i$.

Refractoriness—refractoriness refers to the inability of a nerve fiber to discharge multiple times in rapid succession. If two or more stimulus events are presented in rapid succession, the corresponding sequence of response waveforms may exhibit decrements or fluctuations in magnitude among successive waveforms, or in some cases a complete absence of some responses. Refractoriness may be characterized by the relationship between inter-pulse interval and stimulus intensity threshold for eliciting a second, third or nth response. Alternatively, it may be characterized by the relationship between inter-pulse interval and the decrement in magnitude (or latency) between successive response waveforms. Many other parametric relationships may also be readily defined to characterize refractoriness.

One possible way of quantifying the property of refractoriness is to consider that it can be characterized by the parameter W in the equation:

$$M(t)=Mo(1-e^{(t+a)/W})$$

Where 'a' and 'W' are determined by a curve fitting procedure which minimizes the error between the function M(t)

and a sequence of 'n' response magnitudes $M_1$ $M_2$ ... Mn. Those magnitudes are determined by presenting 'n' pairs of identical stimuli, with delays $t_1$ and $t_2$ ... $t_n$ between the two stimuli of each pair. Each magnitude Mi is the magnitude of the second response elicited from a given pair, and Mo is the magnitude of the first response (which does not vary the delay).

Stimulus following—generally, when the intensity of a single stimulus pulse is increased (between the limits of response threshold and response saturation) the magnitude of the corresponding response waveform increases.

However, due to complex interactions of refraction and integration, when multiple stimulating pulses occur in rapid succession and with varying intensity, the correspondence between pulse intensity and response magnitude may not be preserved. As a result, the extent to which the envelope of response magnitudes follows the envelope of pulse intensities may vary with the inter-pulse interval (or equivalently, pulse rate). Stimulus following may be characterized by the measured relationship between inter-pulse interval and ratio of stimulus intensity modulation depth to response waveform magnitude modulation depth. An alternative measure of stimulus following has been described by Wilson et al Research Triangle Institute NIH Contract No. 1-DC-5-2103 Quarterly Progress Report 7: Feb. 1 through Apr. 30, 1997. Those investigators described waxing and waning of response magnitudes in response to successive equal intensity pulses. The magnitude of the alteration and its relationship to inter-pulse interval has been used to characterize stimulus following. Stimulus following may be also characterized using a series of pulses in which only one pulse differs in intensity from the others, which produces a singularly larger or smaller response magnitude. Many other parametric relationships may also readily defined to characterize Stimulus Following.

One possible way of quantifying the property of Stimulus Following is to consider that it can be characterized by the relationship:

$F=D_2/D_1$ where $D_1$ is the depth-of-modulation of an aptitude modulated pulse train, and $D_2$ is the depth-of-modulation of train of elicited responses. Depth-of-modulation is defined as follows:

$D1=1-(I_{min}/I_{max})$ where $I_{max}$ is the intensity of the strongest pulse in the train, and $I_{MIN}$ is the intensity of the weakest pulse.

$D2=1-(M_{min}/M_{max})$ where $M_{max}$ is the magnitude of the largest response, and $M_{min}$ is the magnitude of the smallest response.

With regard to the second considered category of neural response properties, spatial properties of the neural response are determined from spatial distances between stimulating and/or recording electrodes. Often, these properties are also characterized by response waveform magnitude and its dependence on such distances, or on stimulus intensity, or both. For a given set of conditions (for example electrode sets, pulse width, pulse rate) the relationship between stimulus intensity and corresponding measured response magnitude is referred to as input-output or I/O function. Examples of spatial properties and possible relationships which may be used to quantify each of these properties include:

Spread of Excitation—

Spread of Excitation refers to the extent to which a stimulus which is delivered at a single site within the cochlea excites nerve fibers not only near the site, but also at various distances from the site. When the stimulus is delivered at a single site (through a fixed electrode set), recordings of the response may be made through various electrode sets at different distances from the stimulating electrode set (either simultaneously, or sequentially by repeating the stimulus). Spread of Excitation may be characterized by the relationship between response magnitude and distance of the recording site from the stimulating site. The process may be repeated for many stimulus intensities such that a full I/O function is measured at each recording site. In this case, Spread of Excitation may be characterized individually at each intensity or by the relationship between some feature of I/O curve (for example threshold or mid-point or slope) and distance. Similarly, Spread of Excitation may be measured by fixing the position of the recording site, and presenting stimulation through electrodes at various distances from the recording site. Many other parametric relationships may be also readily defined to characterize Spread of Excitation.

One possible way of quantifying the property of Spread of Excitation is to consider that it can be characterized by the parameter Z in the equation $M(x)=Ae-x/Z$ where A and Z are determined by a curve fitting procedure which minimizes the error between function Mx and a sequency of n response magnitudes $M_1, M_2, ... Mn$ measured at n recording sites located at distances $x_i, x_2 ... xn$ from the Stimulus Site. Parameter Z is sometimes referred to as a "space constant".

Overlap of Stimulation—given that stimulation may spread to varying distances from the stimulating electrodes (depending on stimulus intensity and electrode geometry), some nerve fibers may fall within regions where they are subject to simulation by currents from multiple stimulating electrodes sets. Thus, when stimuli are simultaneously delivered by two or more sets, those nerve fibers may experience complex combinations of stimuli which have additive or cancelling effects on the net excitation. The existence of such regions of overlap often referred to as "channel interaction". It limits the independence of stimuli delivered through separate electrode sets which are to be intended to act discretely upon isolated groups of nerve fibers. Overlap of stimulation may be characterized by the relationship between response magnitude, intensities and polarities of stimulation through two or more electrode sets, and the distances among the stimulating electrode set. Many other parametric relationships may also be readily defined to characterize overlap of stimulation.

One possible way of quantifying the property of Overlap of Stimulation is to consider that it can be characterized by $O=(I_2-I_1)/I_1$, where I is the threshold intensity required to elicit a response to a first stimulus delivered through a first electrode set when the first stimulus is presented alone, and $I_2$ is the threshold intensity for a stimulus delivered through the first electrode set when a second stimulus is delivered concurrently through a second electrode set.

Density of Innervation—density of innervation refers to the number of surviving nerve fibers (or cell bodies) per unit of volume or distance at any particular point in the cochlea. Many etiologies of deafness result in non-uniform neural survival, such that the density of innervation is "patchy" or inconsistent at various intervals within the cochlea. The magnitude of the response depends upon in part on the number of activated nerve fibers so it can be used to infer an estimate of local innervation density. By comparing response magnitudes with stimuli delivered at various sites, or recordings at various sites, or both, local innervation density may be estimated. Density of innervation may be characterized by the relationship between response magnitude and recording site (or stimulating sites, or both). Similarly, density of innervation may be characterized by the relationship between a particular feature of the I/O function (for example threshold, slope) and the recording site (or stimulating site, or both).

One possible way of quantifying the property of Density of Innervation is to consider that it can be characterized by S in the following equation:

$$M(I)=SI+\rho$$

where S and $\rho$ are determined by a linear regression through a sequence of n response magnitudes $M_1, M_2, \ldots M_n$ measured at n corresponding stimulus intensities $I_1, I_2 \ldots I_n$.

As discussed above, the third category of neural response properties is spatial-temporal properties. Spatial-temporal properties include those properties of the neural response which vary with both timing (as described with reference to temporal properties above) and the selection of stimulation or recording electrode sites (as described with reference with spatial properties). As such, they comprise the combination of
1. temporal properties described above in the circumstance where the presumption of fixed stimulus and recording site is removed and
2. spatial properties described above in which the presumption of simultaneous stimulation at two or more sites is removed.

Masking—masking refers to the influence of a second (masking) stimulus on the response which is otherwise elicited by a first (probe) stimulus. For brevity, we use the term masking to describe either a decrement in the response of the probe (traditional usage) or increment in the response to the probe (sometimes described as "facilitation"). The influence of interest may be either a modification of the response magnitude or the response latency.

When both masker and probe are delivered through a single set of stimulating electrodes at different moments in time, this is a manifestation of refractoriness or integration as described above. Also, when both masker and probe are delivered simultaneously through different electrode sets, this relates to overlap of stimulation which is also described above. However, it is also possible to deliver (two or more) stimuli non-simultaneously to different electrode sets. The resulting influence of the masker on the response to the probe represents a measure of spatial-temporal interaction. Masking can be characterized by the multi dimensional dependence of magnitude (or latency) of the probe response upon:
a) the distance between stimulating electrode sets;
b) the separation in time of the masker and probe;
c) intensity of the masker;
d) the intensity of the probe; and
e) the distances between the recording electrodes and the stimulating electrode sets.

Masking can be extended to incorporate stimuli by two or more electrode sets, each receiving different stimuli, with arbitrary timing relationships among maskers and probe. In addition, the masker stimulus can be a single pulse, or arbitrary complex train of pulses. In its generalized form, masking subsumes the properties of refractoriness and integration when either is characterized using more than a single set of stimulating electrodes.

One possible way of quantifying the property of Masking is to consider that it can be characterized by the following equation:

$M=(I_2-I_1)/I_1$ where $I_2$ AND $I_1$ are as defined above for Overlap of Stimulation. In this case, the first and second stimuli are separated in time by a specified delay.

Interleaving—trains of stimuli which are presented non-simultaneously to two or more sets of stimulating electrodes are often described as "interleaved". Stimulus Following as described above may be characterized using such interleaved stimuli with responses recorded at one or more sites. The metric of Stimulus Following may vary with distances among electrodes as well as repetition rate and recording location.

As outlined above, a large set of response properties can be measured, each of which gives insight into the capacities of the individual's auditory periphery. The decision about which parameters to optimize from which properties may vary from individual to individual. However, the process by which such properties guide parameter selection can be described.

Strategy Selection

Speech processing strategies are distinguished in part by the manner in which speech signals are encoded. For example, CIS (Continuous Interleaved Sampling) uses pulses at relatively high rates delivered through relatively few widely spaced electrodes to represent speech, whereas SPEAK uses relatively low rates and a relatively large number of closely spaced electrodes.

Therefore, SPEAK would be preferred over CIS if response properties show evidence of poor neural behavior at high pulse rates (for example such as slow recovery from refractoriness, long integration time, poor stimulus following at high rates). Conversely, CIS would be preferred if response properties show evidence of poor spatial selectivity (broad spread of stimulus, large overlap of stimulation). Similarly, any strategy which is vulnerable to channel interaction (SAS—Simultaneous Analogue Stimulations) should be avoided if there is substantial overlap of stimulus. Therefore, by measuring neural response properties, the most optimal speech processing strategy can be selected to provide the most benefit to the individual.

The following examples illustrate relationships which may be used to optimize strategy selection based on measure neural response properties. It should be appreciated that these relationships are exemplary only and other similar optimizing relationships may be further defined which still fall within the scope of the present invention.
1. A high rate strategy (CIS or ACE) may be selected if the mean refractoriness value W computed for two or more electrodes falls below a threshold value $W_{max}$. Otherwise, a low rate strategy (SPEAK) may be selected.
2. A strategy utilizing many electrodes (SPEAK, ACE) may be selected if the mean overlap measure $O_{avg}$ falls below a threshold value $O_{max}$. Otherwise a strategy utilizing fewer electrodes (for example CIS) may be selected.
3. A composite parameter which includes weighted contributions from measures of overlap, refractoriness, Stimulus Following and Spread of Excitation may be defined: $C=aO+bW+cF+dS$, where a, b, c and d are predetermined constants. Such a composite parameter may be used in place of individual parameters and compared against similarly defined predetermined threshold values.

Parametric Optimization

Within the parametric space of a given strategy, individual parameters may be optimized based on neural response properties. The ACE strategy provides many options for rate and number of electrodes. Measures of spatial-temporal interaction (for example masking) can identify the optimum trade off between rate and channel-spacing to avoid exceeding the temporal capacity of nerves. In general, for pulse style strategies, Refractoriness, Integration and Stimulus Following measures can identify the highest rate which can be employed without exceeding peripheral capacity. Innervation density can be used to identify electrodes which should be excluded from the MAP due to lack of proximate target neurons. Spatial-temporal measures such as masking can determine the optimum electrode sequence order (stagger order) to minimize channel interactions with sequential pulse strategies. In cases where the number of available number of electrodes exceeds the number required for a particular strategy, temporal response properties can identify the optimal subset of electrodes which will be effective with high rate stimulation, while spatial properties can identify electrodes to be avoided due to excessive stimulus overlap.

The following examples illustrate relationships which may be used for electrode selection and parametric optimization based on measure neural response properties. It should be appreciated that these relationships are exemplary only and other similar optimizing relationships may be further defined which still fall within the scope of the present invention.

Electrode Selection:

1. An electrode may be excluded from a patient map if the corresponding measure of innovation density S falls below a threshold value $S_{min}$.

2. An electrode may be excluded from a high-rate map if it exhibits poor ability to follow a high-rate stimuli as evidenced by:
Refractoriness W which exceeds a threshold value $W_{max}$
Stimulus Following which falls below a threshold value $F_{min}$ for a predetermined pulse rate.

3. Electrode may be excluded from a map if they exhibit overlapping stimulation which exceeds a threshold value $O_{max}$ at a predetermined stimulus intensity I.

Parametric Optimization:

1. Stagger order (the sequence with which electrodes are selected for stimulation). May be optimized by selecting a sequence which minimizes the sum of stimulus overlap measures O or masking measures M across successive sites in the sequence.

2. Stimulus rate may be optimized by determining the highest rate for which the mean measure of refraction $W_{avg}$ falls below a threshold value $W_{max}$. Alternatively, stimulus rates may be determined individually for each electrode by comparing the individual measure W for each electrode against a similar threshold.

3. When stimulus rates and number of electrodes to be used are subject to a combined limit (for example, an aggregate rate imposed by the prosthesis), the trade-off between rates and number of electrodes may be optimized by selecting from among available rate/electrode combinations that combination which minimizes the mean masking measure M.

4. The intensity of a conditioning stimulus may be determined from the minimum intensity which yields a Stimulus Following measure F which exceeds a predetermined threshold value $F_{min}$.

5. The rates of a conditioning stimulus may be determined by selecting the rate which maximizes the Stimulus Following measure F.

Conditioner Tuning

Recently, it has been proposed that addition currents be exploited in addition to those introduced to represent the sound stimulus itself. These addition currents are described as "conditioners" whose purpose is to introduce stochastic variability in the neural discharges, more closely mimicking the natural hearing process. Conditioners are generally envisioned to take the form of high rate pulse trains or analogue noise current. Stimulus following has been proposed as metric of merit for assessing the effect of conditioners. Therefore, measurement of stimulus following may be used to determine the optimum intensity, rate, spectral content or spatial distribution of conditioning stimuli for an individual.

The remaining discussion will provide a more detailed description of one particular application of the present invention, namely the optimization of stimulation rate in response to various parameters derived from neural response as described above.

According to one embodiment of the present invention a subject implanted with a cochlear implant prosthesis incorporating an NRT system is stimulated to evoke at least one neural response measured in respect of at least one electrode.

Referring now to FIGS. 1A and 1B there are shown neural responses each made from a different patient for an electrode located at approximately the same position relative to the patient's cochlea. It will be noted that the shape of the waveform that has been elicited differs from patient to patient.

Neural response waveforms include typical identifiable features. For example, N1 denotes the first negative peak of the neural response. P1 denotes the first positive peak of the neural response while P2 denotes the second positive peak.

The present method is based on the inventors' discovery that the various parameters associated with a neural response waveform may be used to predict those patients which will benefit from a high-rate stimulation strategy, for example a strategy applying stimulations at 1200 Hz and above (such as the aforementioned ACE strategy), as compared with those who do not so benefit but are better suited to a low rate strategy, for example one applying stimulations at 250 Hz (such as the previously referred to SPEAK strategy).

A preferred parameter for use in determining a desired stimulation rate is a latency associated with a given neural response waveform. However, other parameters, such as EP amplitude, I/O function parameters (e.g. threshold or slope) and refraction curve properties may be used to determine appropriate stimulation rates. As has been previously described, it will be understood that appropriate relationships between these parameters and the desired stimulation rate may be determined empirically as is well within the skill of the person skilled in the art.

The time period between the occurrence of P1 and N1 is one such latency. Another is the time period between the application of stimulation and the occurrence of N1, P1, or P2. Other latency periods may also be calculated with reference to other identifiable waveform features. In particular the inventors have discovered that the longer the latency period the lower the rate of stimulation indicated to be appropriate, whereas if the latency period is shorter then the use of a higher rate stimulation is indicated in order to improve the benefit of the therapy conferred by the cochlear prosthesis.

Referring again to FIG. 1 it will be noted that patient LH exhibits a T (P1)–T (N1) latency of 200-300, μs whereas patient GZ exhibits a T (P1)–T (N1) latency of 400-500, μs. Using the latency value as an argument in a mathematical function, an optimized stimulation rate can be determined. Several mathematical functions R=f(Δ) are available where R is the optimized rate and Δ is a latency period derived from the neural response waveform. For example one very simple model is: If Δ<K then R=A, else R=B where A>B and K is a constant. Such a model is used where two stimulation rates, A and B, are available and K is a predetermined constant. Another model might be that R=(c1/Δ)+c2 where c1 and c2 are constants.

The constants K, c1, c2 of the above models are derived by reference to patients whose optimal stimulation rates have been found by means of prior art methods. For example, for the first method where A is the time between the occurrence of N1 and P1, A=250 Hz and B=1200 HZ then a value of K=350 us has been found to be suitable. For the second method the values c1=2850 Hz and c2=−225 μs have been suitable where, once again, the latency period has been measured between N1 and P1. It will be understood by the person skilled in the art that these functions are only illustrative of the type of relationships that may be suitable and that many other functions may be equally defined to establish the relationship.

For example, one method of defining a suitable function is by examination of latency-to-optimal-rate relationships measured empirically with another optimization means.

Figure 2:
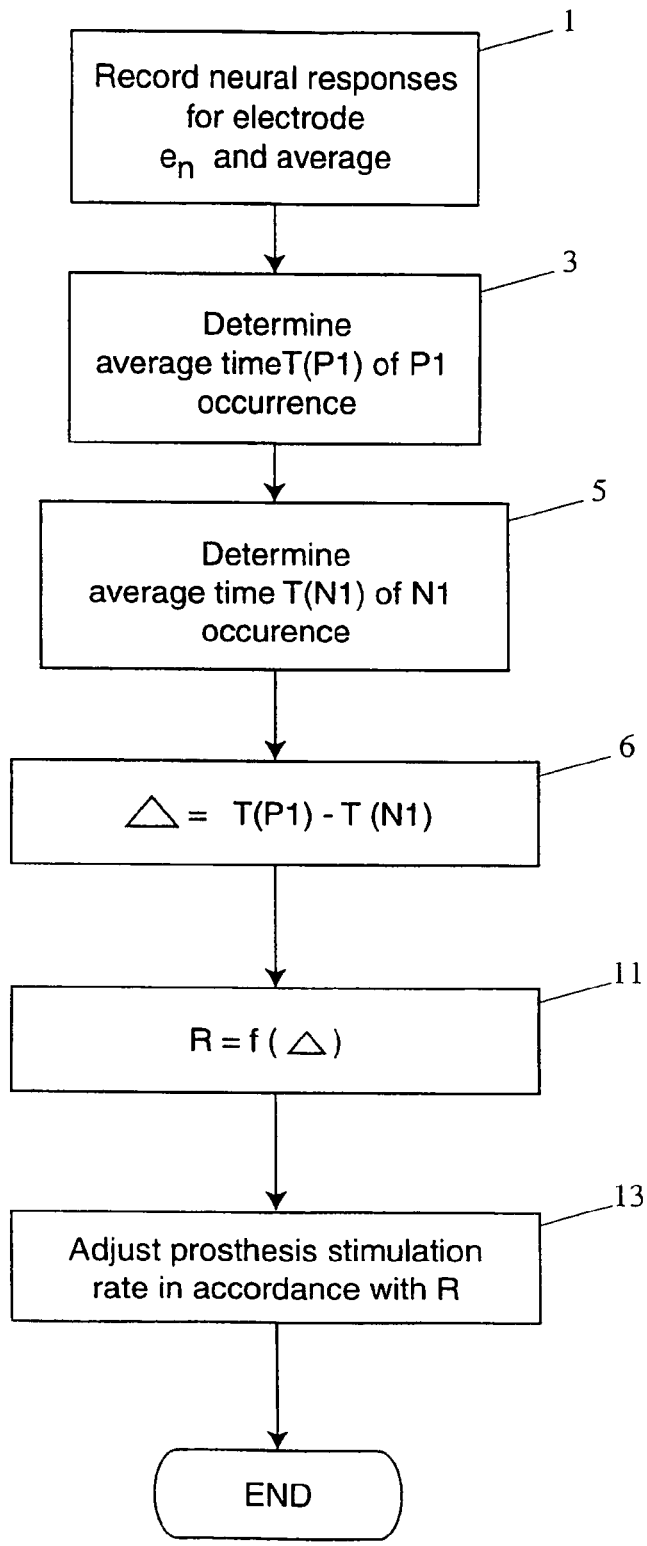
FIG. 2 is a flowchart of a method according to the present invention.

Referring now to FIG. 2 the steps of the method according to the previously described embodiment are specified. Initially the patient's neural response in respect of a selected electrode is recorded. Preferably a number of neural responses are recorded and averaged as shown at box 1. The averaged waveform is then processed to determine the time T (P1) at which the first positive peak, P1, occurs. Methods for making such a determination are well known in the fields of numerical mathematics and computer science and so will not be described in detail here. Similarly at box 5 the time T (N1) at which the first negative peak occurs is determined and stored. At box 6 the difference, A, between T (P1) and T (N1) is calculated and stored. While the latency value A that has been used in the present example comprises T (P1)–T (N1) as has been previously mentioned other values for latency could be calculated such as T (P1)–T (stim), T (N1)–T (stim) or T (P2)–T (stim) although in each case the aforementioned values of K, c1 and c2 would have to be re-determined. At box 11 the value of $\Delta$ calculated in box 6 is used as an argument in the function R=f($\Delta$) and so an optimal stimulation rate is calculated.

While the above embodiment relates to determining a stimulation rate in respect of only one electrode, in a further embodiment the determination of latency periods is made for all of the electrodes, or at least for a number of electrodes taken over the apical to basal range of positions. The latency differences are then combined, for example by averaging or taking the overall maximum, and processed as explained previously.

Furthermore, it will be appreciated that a rate derived at, for example, electrode N, need not necessarily be applied to electrode N, but may be applied to its neighboring electrodes and/or all available electrodes. Similarly, if M latencies are measured, they may be used to calculate M or fewer rates, to be distributed among any number of electrodes.

Figure 3:
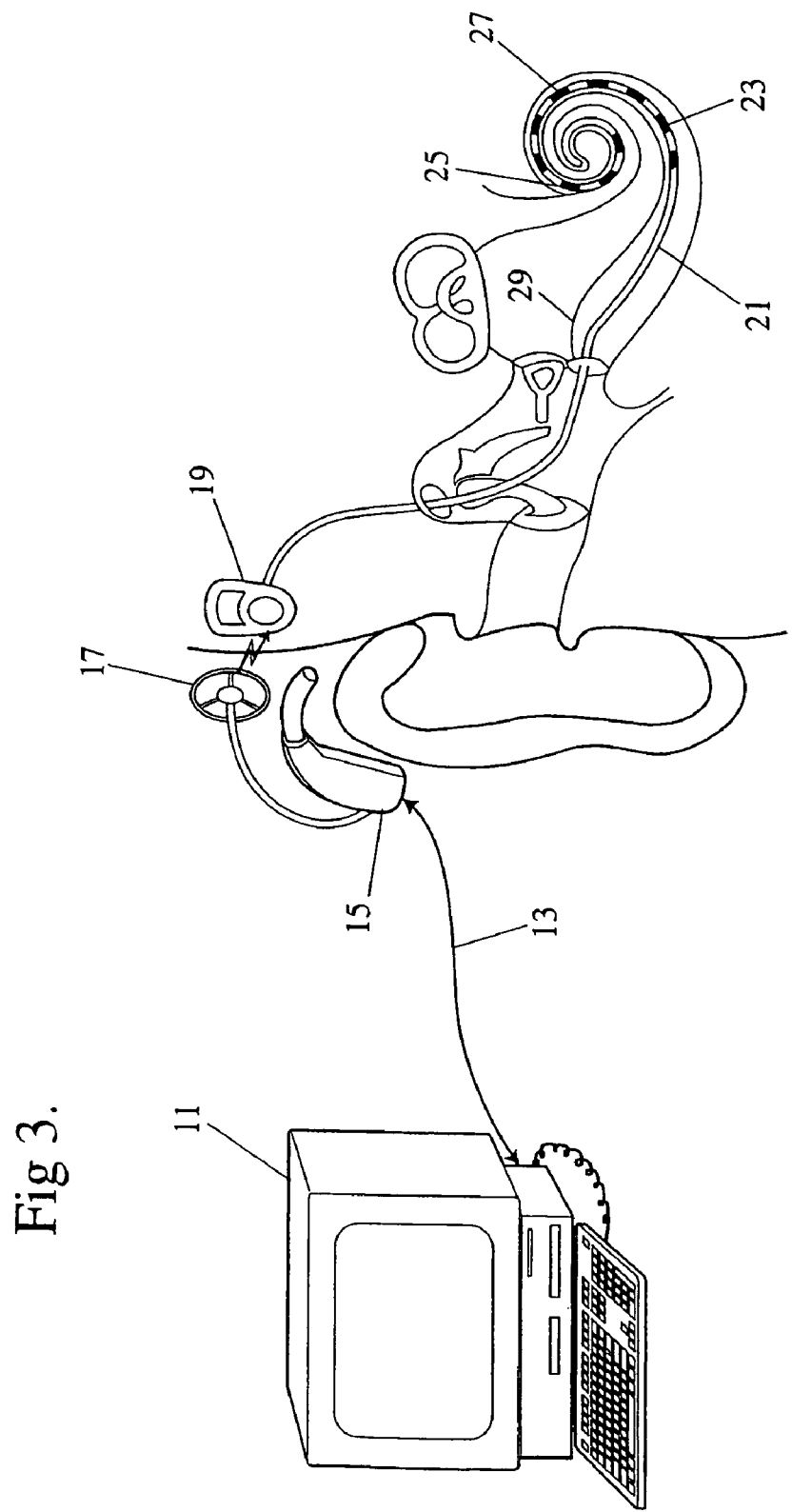
FIG. 3 is a schematic diagram of an apparatus for adjusting or selecting between stimulation strategies of a cochlear implant prosthesis according to the present invention.

Referring now to FIG. 3 there is depicted an apparatus for practicing the previously described method. Computer 11 is programmed to carry out the steps illustrated by the flowchart of FIG. 2. The computer is bi-directionally coupled by means of data-link 13 to speech processor 15.

Speech processor 15 is in communication with the implanted portion of the cochlear prosthesis (which includes behind-the-ear processor 15, transmit antenna 17, receiver stimulator 19 and electrode array 21) by means of an inductive link established between transmit antenna 17 and the receive antenna of the receiver stimulator 19. Processor 15 includes non-volatile memory which holds several different speech processing and stimulation strategy programs.

In carrying out the inventive method computer 11 firstly instructs processor 15 to stimulate the auditory system by means of a selected electrode of electrode array 21, electrodes 25, 27 and 23 are identified in FIG. 13. The stimulation command is encoded and transmitted as an RF signal to receiver stimulator 19 where it is decoded and a stimulation current applied by means of the selected electrode. The electrical activity of the auditory system evoked in response to the stimulation, i.e. the neural response, is then detected, encoded and transmitted back to processor 15 by means of the inductive link.

At least one neural response waveform, and preferably several for purposes of averaging, are generated and transmitted from processor 15 to computer 11 by means of link 13.

Computer 11 is programmed to operate upon the received data and to determine an optimal stimulation rate as previously described in reference to FIG. 2. Computer 11 sends a command signal and data signal relating to the optimal data rate to processor 15, which then adjusts its stimulation strategy to accord with the determined optimal rate.

As previously mentioned with reference to FIG. 2, according to a further embodiment latency periods are calculated by computer 11 for a number of electrodes, for example for apical electrode 25, electrode 27 and basal electrode 23. The latency periods are then combined, for example averaged or the largest value selected, and the combined value is compared with a predetermined figure as previously explained. The result of the comparison is then transmitted via link 13 to processor 15. In the event that a high rate stimulation strategy, e.g. ACE is indicated as being beneficial to the patient then processor 15 downloads such a strategy from its non-volatile memory.

It will be further understood by those skilled in the art that the exact demarcation of tasks carried out by computer 11 and by processor 15 does not have to be as explained with reference to the previous embodiment.

For example, in a further embodiment processor 15 incorporates sufficient computational means to execute a program according to the flowchart of FIG. 2, preloaded into internal memory, so that the stimulation rate adjustment can be carried out without recourse to equipment external to the cochlear prosthesis.

While the invention has been explained with reference to a limited number of examples further embodiments and variations are possible and will be apparent to those skilled in the art. Accordingly the following claims are intended to be constructed broadly and not merely restricted to the embodiments described herein.

The claims defining the invention are as follows:

1. A method for optimizing a speech processing strategy configured to convert a speech signal into an electrical stimulation signal in a cochlear implant having one or more electrodes implanted in an inner ear of a patient, the method comprising:
    measuring with said one or more electrodes at least one spatial property of a neural response of the inner-ear of the patient; and
    adjusting a strategy parameter of said speech processing strategy based on said at least one neural response property.

2. The method of claim 1, wherein said strategy parameter comprises a parameter intrinsic to said speech processing strategy that affects the representation of said speech signal by said stimulation signal.

3. The method of claim 1, wherein said adjusting said strategy parameter comprises:
    varying the sequence in which stimulation will be delivered to said one or more electrodes so as to minimize interaction between stimulation pulses of said stimulation.

4. The method of claim 1, wherein said one or more electrodes comprise a plurality of electrodes, and wherein said adjusting said strategy parameter comprises:
    selecting which of said plurality of electrodes will be used to deliver said stimulation to the recipient.

5. The method of claim 1, wherein said adjusting said strategy parameter comprises:
selecting a rate at which stimulation will be delivered to said one or more electrodes of said cochlear implant.

6. The method of claim 1, wherein said measuring said at least one neural response property comprises:
providing at least one electrical stimulus to the inner-ear of the patient with at least one of said one or more electrodes;
recording a time-varying electrical potential within the inner-ear via at least one of said one or more electrodes; and
determining said at least one property of said neural response from said recorded time varying electrical potential.

7. The method of claim 6, wherein said time-varying electrical potential is recorded in one or more of the cochlea nucleus or auditory nerve.

8. The method of claim 6, wherein said at least one electrode used to record said time-varying electrical potential is the same at least one electrode used to provide said at least one electrical stimulus.

9. The method of claim 6, wherein said at least one electrical stimulus provided to the inner-ear may be varied depending on a neural response property to be measured.

10. The method of claim 1, wherein said measuring said at least one spatial neural response property comprises delivering an electrical stimulus to the inner-ear, and wherein said spatial property is the spread of said electrical stimulus.

11. The method of claim 1, wherein said cochlear implant further includes a processor integrated therein, said processor configured to measure said at least one neural response property and adjust said strategy parameter based on said measured at least one neural response property.

12. A method for optimizing a conditioning stimulus delivered via one or more electrodes implanted in an inner ear of the patient, the method comprising:
measuring with said one or more electrodes at least one property of a neural response of the inner-ear of the patient; and
adjusting said conditioning stimulus so as to maximize stochastic variability provided by said conditioning stimulus based on said at least one neural response property.

13. The method of claim 12, wherein said adjusting said conditioning stimulus comprises:
adjusting the intensity of said conditioning stimulus based on said at least one neural response property.

14. The method of claim 12, wherein said adjusting said conditioning stimulus comprises:
adjusting the rate of said conditioning stimulus based on said at least one neural response property.

15. The method of claim 12, wherein measuring said at least one neural response property comprises:
providing at least one electrical stimulus to the inner-ear of the patient with at least one of said one or more electrodes;
recording a time-varying electrical potential within the inner-ear via at least one of said one or more electrodes; and
determining said at least one property of said neural response from said recorded time varying electrical potential.

16. The method of claim 15, wherein said time-varying electrical potential is recorded in one or more of the cochlea nucleus or auditory nerve.

17. The method of claim 15, wherein said at least one electrode used to record said time-varying electrical potential is the same at least one electrode used to provide said at least one electrical stimulus.

18. The method of claim 15, wherein said at least one electrical stimulus provided to the inner-ear may be varied depending on a neural response property to be measured.

19. The method of claim 12, wherein said at least one neural response property is a temporal property of said neural response.

20. The method of claim 19, wherein said temporal property is a latency period between an occurrence of a first identifiable feature of said neural response to an occurrence of a second identifiable feature of said neural response.

21. The method of claim 12, wherein said at least one neural response property is a spatial property of said neural response.

22. The method of claim 21, wherein said measuring said at least one neural response property comprises delivering an electrical stimulus to the inner-ear, and wherein said spatial property is the spread of said electrical stimulus.

23. The method of claim 12, wherein said at least one neural response property is a spatio-temporal property of said neural response.

24. The method of claim 23, wherein said measuring said at least one neural response property comprises delivering at least first and second stimuli, and wherein said spatial property comprises the influence of said second stimuli on said response resulting from said first stimuli.

25. The method of claim 1, wherein said cochlear implant further includes a processor integrated therein, said processor configured to measure said at least one neural response property and adjust said conditioning stimulus based on said measured at least one neural response property.

26. A method for selecting one of a plurality of speech processing strategies each of which converts speech signals into electrical stimulation signals in a cochlear implant having one or more electrodes implanted in an inner ear of a patient, the method comprising:
measuring with said one or more electrodes at least one property of a neural response of the inner-ear of the patient; and
selecting one of said plurality of speech processing strategies based on said at least one neural response property, wherein said at least one neural response property is a spatial property of said neural response.

27. The method of claim 26, wherein said selecting said speech processing strategy comprises:
selecting a speech processing strategy configured to convert an input speech signal into an electrical stimulation signal having a high pulse rate.

28. The method of claim 26, wherein said selecting a speech processing strategy comprises:
selecting a speech processing strategy configured to convert an input speech signal into an electrical stimulation signal having a low pulse rate.

29. The method of claim 26, wherein said measuring said at least one neural response property comprises:
providing at least one electrical stimulus to the inner-ear of the patient with at least one of said one or more electrodes;
recording a time-varying electrical potential within the inner-ear via at least one of said one or more electrodes; and
determining said at least one property of said neural response from said recorded time varying electrical potential.

30. The method of claim 29, wherein said time-varying electrical potential is recorded in one or more of the cochlea nucleus or auditory nerve.

31. The method of claim 29, wherein said at least one electrode used to record said time-varying electrical potential is the same at least one electrode used to provide said at least one electrical stimulus.

32. The method of claim 29, wherein said at least one electrical stimulus provided to the inner-ear may be varied depending on a neural response property to be measured.

33. The method of claim 26, wherein said measuring said at least one neural response property comprises delivering an electrical stimulus to the inner-ear, and wherein said spatial property is the spread of said electrical stimulus.

34. The method of claim 26, wherein said cochlear implant further includes a processor integrated therein, said processor configured to measure said at least one neural response property and to select said speech processing strategy based on said measured at least one neural response property.

35. A method for selecting one of a plurality of speech processing strategies each of which converts speech signals into electrical stimulation signals in a cochlear implant having one or more electrodes implanted in an inner ear of a patient, the method comprising:
measuring with said one or more electrodes at least one property of a neural response of the inner-ear of the patient; and
selecting one of said plurality of speech processing strategies based on said at least one neural response property, wherein said at least one neural response property is a spatio-temporal property of said neural response.

36. The method of claim 35, wherein said selecting said speech processing strategy comprises:
selecting a speech processing strategy configured to convert an input speech signal into an electrical stimulation signal having a high pulse rate.

37. The method of claim 35, wherein said selecting a speech processing strategy comprises:
selecting a speech processing strategy configured to convert an input speech signal into an electrical stimulation signal having a low pulse rate.

38. The method of claim 35, wherein said measuring said at least one neural response property comprises:
providing at least one electrical stimulus to the inner-ear of the patient with at least one of said one or more electrodes;
recording a time-varying electrical potential within the inner-ear via at least one of said one or more electrodes; and
determining said at least one property of said neural response from said recorded time varying electrical potential.

39. The method of claim 38, wherein said time-varying electrical potential is recorded in one or more of the cochlea nucleus or auditory nerve.

40. The method of claim 38, wherein said at least one electrode used to record said time-varying electrical potential is the same at least one electrode used to provide said at least one electrical stimulus.

41. The method of claim 38, wherein said at least one electrical stimulus provided to the inner-ear may be varied depending on a neural response property to be measured.

42. The method of claim 35, wherein said measuring said at least one neural response property comprises delivering at least first and second stimuli, and wherein said spatial property comprises the influence of said second stimuli on said response resulting from said first stimuli.

43. The method of claim 35, wherein said cochlear implant further includes a processor integrated therein, said processor configured to measure said at least one neural response property and to select said speech processing strategy based on said measured at least one neural response property.

44. A method for optimizing a speech processing strategy configured to convert a speech signal into an electrical stimulation signal in a cochlear implant having one or more electrodes implanted in an inner ear of a patient, the method comprising:
measuring with said one or more electrodes at least one spatio-temporal property of a neural response of the inner-ear of the patient; and
adjusting a strategy parameter of said speech processing strategy based on said at least one neural response property.

45. The method of claim 44, wherein said strategy parameter comprises a parameter intrinsic to said speech processing strategy that affects the representation of said speech signal by said stimulation signal.

46. The method of claim 44, wherein said adjusting said strategy parameter comprises:
varying the sequence in which stimulation will be delivered to said one or more electrodes so as to minimize interaction between stimulation pulses of said stimulation.

47. The method of claim 44, wherein said one or more electrodes comprise a plurality of electrodes, and wherein said adjusting said strategy parameter comprises:
selecting which of said plurality of electrodes will be used to deliver said stimulation to the recipient.

48. The method of claim 44, wherein said adjusting said strategy parameter comprises:
selecting a rate at which stimulation will be delivered to said one or more electrodes of said cochlear implant.

49. The method of claim 44, wherein said measuring said at least one neural response property comprises:
providing at least one electrical stimulus to the inner-ear of the patient with at least one of said one or more electrodes;
recording a time-varying electrical potential within the inner-ear via at least one of said one or more electrodes; and
determining said at least one property of said neural response from said recorded time varying electrical potential.

50. The method of claim 49, wherein said time-varying electrical potential is recorded in one or more of the cochlea nucleus or auditory nerve.

51. The method of claim 49, wherein said at least one electrode used to record said time-varying electrical potential is the same at least one electrode used to provide said at least one electrical stimulus.

52. The method of claim 49, wherein said at least one electrical stimulus provided to the inner-ear may be varied depending on a neural response property to be measured.

53. The method of claim 44, wherein said measuring said at least one spatio-temporal neural response property comprises delivering at least first and second stimuli, and wherein said spatial-temporal property comprises the influence of said second stimuli on said response resulting from said first stimuli.

54. The method of claim 44, wherein said cochlear implant further includes a processor integrated therein, said processor configured to measure said at least one neural response property and adjust said strategy parameter based on said measured at least one neural response property.

55. The method of claim 44, wherein said cochlear implant further includes a processor integrated therein, said processor configured to measure said at least one neural response property and adjust a conditioning stimulus based on said measured at least one neural response property.

\* \* \* \* \*